(12) United States Patent
Garst

(10) Patent No.: US 6,254,860 B1
(45) Date of Patent: Jul. 3, 2001

(54) OCULAR TREATMENT USING CYCLOSPORIN-A DERIVATIVES

(75) Inventor: Michael E. Garst, Newport Beach, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/290,833

(22) Filed: Apr. 13, 1999

(51) Int. Cl.[7] .................................................. A61K 31/74
(52) U.S. Cl. ............................................................ 424/78.04
(58) Field of Search .................................... 424/78.04, 427

(56) References Cited

U.S. PATENT DOCUMENTS

| 4,649,047 | 3/1987 | Kaswan . |
|---|---|---|
| 4,839,342 | 6/1989 | Kaswan . |

FOREIGN PATENT DOCUMENTS

| WO 89/01772 | 3/1989 | (WO) | ............................... A61K/9/00 |
| WO 9828328 | 7/1998 | (WO) . | |
| WO 9828329 | 7/1998 | (WO) . | |
| WO 9828330 | 7/1998 | (WO) . | |

*Primary Examiner*—Carlos A. Azpuru
(74) *Attorney, Agent, or Firm*—Walter A. Hackler

(57) ABSTRACT

A method of treating a disorder in an eye, for example, an aqueous deficient dry eye state, phacoanaphylactic endophthalmitis, or uveitis, is provided. The method generally includes administering a therapeutically effective amount of a certain cyclosporin A derivative topically to the affected eye. The derivative may be administered as a solution, suspension or ointment in a pharmaceutically acceptable excipient.

10 Claims, No Drawings

OCULAR TREATMENT USING CYCLOSPORIN-A DERIVATIVES

The present invention generally relates to treatment of ocular diseases and disorders and more specifically relates to a method for treatment of aqueous deficient dry-eye state, phacoanaphylaxis endophthalmitis and uveitis using certain cyclosporin derivatives.

The exposed part of a normal eye is covered by a thin tear film. The presence of a continuous tear film is important for the well-being of the corneal and conjunctival epithelium and provides the cornea with an optically high quality surface. In addition, the aqueous part of the tear film acts as a lubricant to the eyelids during blinking of the lids. Furthermore, certain enzymes contained in the tear fluid, for example immunoglobin A, lysozyme and beta lysin, are known to have bacteriostatic properties.

A sound lacrimal system functions to form and maintain a properly structured, continuous tear film. The lacrimal apparatus consists of the secretory system (the source), the distribution system, and the excretory system (the sink). In the secretory system, aqueous tears are supplied by main and accessory lacrimal glands. The bulk of the tear film is made of such aqueous tear. The continuous production and drainage of aqueous tear is important in maintaining the corneal and conjunctival epithelium in a moist state, in providing nutrients for epithelial respiration, in supplying bacteriostatic agents and in cleaning the ocular surface by the flushing action of tear movement.

Abnormalities of the tear film include an absolute or partial deficiency in aqueous tear production (keratoconjunctivitis sicca, or KCS).

In relatively mild cases, the main symptom of KCS is a foreign body sensation or a mild scratchiness. This can progress to become a constant, intense burning or irritative sensation that can be debilitating to a patient.

More severe forms can progress to the development of filamentary keratisis, a painful condition characterized by the appearance of numerous strands or filaments attached to the corneal surface. Evidence suggests that these filaments represent breaks in the continuity of normal corneal epithelial cells. The shear created by lid motion pulls these filaments, causing pain. Management of this stage of KCS is very difficult.

A frequent complication of KCS is secondary infection. Several breakdowns in the eye's normal defense mechanisms seem to occur, presumably attributable to a decrease in the concentration of antibacterial lysozyme in the aqueous tears of a patient suffering from KCS.

Although KCS can develop in the absence of any other overt system abnormality, there is a frequent association of KCS with systemic disease. KCS can occur as part of a larger systemic involvement known as Sjogren's syndrome. This classically consists of dry eyes, dry mouth and arthritis.

Histologically, in KCS (as part of Sjogren's syndrome or in isolation), the initial changes seen in the lacrimal glands are those of focal lymphocytic and plasma cell infiltrates associated with degeneration of glandular tissue. These changes resemble those seen in autoimmune disease in other tissue, giving rise to the speculation that KCS has an autoimmune basis.

Sjogren's syndrome is recognized as an exocrine gland dysfunction. Characteristically, the lacrimal glands show a mononuclear cell infiltration that ultimately leads to destruction of the glandular structure.

Conventional treatment of KCS is symptomatic. Normally, aqueous-deficient dry eye states are treated by supplementation of the tears with artificial tear substitutes. However, relief is limited by the retention time of the administered artificial tear solution in the eye. Typically, the effect of an artificial tear solution administered to the eye dissipates within about thirty to forty-five minutes. Thus, the effect of such products, while soothing initially, does not last long enough. The patient is inconvenienced by the necessity of repeated administration of artificial tear solution in the eye as needed to supplement the normal tears. Moreover, such treatment merely acts to alleviate the symptoms of the dry eye state and does not cure any underlying disorders or causes of the dry eye state.

Histologic studies of the lacrimal glands in patients suffering from Sjogren's syndrome have shown some evidence of lacrimal gland inflammation. Such inflammation may be simply due to the normal aging of the patient. It has been suggested that the use of anti-inflammatory agents might serve to decrease the glandular inflammation. The systemic use of corticosteroids has been advocated in these conditions. However, the merit of systemic corticosteroids in dry eye states has not been established. In most dry eye cases, the hazards of long term use of anti-inflammatory agents would seem to outweigh their potential merit.

Surgical procedures have also been suggested in the management of dry eye states. Where there has been significant conjunctival destruction, mucous membrane transplants have been advocated. It has also been suggested that parotid (saliva) duct transplantation can be useful in the management of dry eyes. However, surgical alterations to combat dry eye conditions constitute a dramatic remedy and any benefit resulting from these alterations is questionable.

It has also been suggested to administer orally a dilute solution of pilocarpine to stimulate the autonomic nervous system to effect increased aqueous tear production. This method of treatment has not met with universal favor because of many unpleasant side effects of ingested pilocarpine.

Animal models of Sjogren's syndrome have been instrumental in basic ophthalmic research. A Sjogren's-like disease has been found in dogs with systemic luperythematosus. This disease, which may be referred to as canine KCS, is a common, chronic, progressive, and potentially blinding disease. A continuum of corneal and conjunctival lesions ensues from the dry eye state. The cause of canine KCS is often not identified. Usually canine KCS is not an isolated ophthalmic disease. It has been speculated in Kaswan et al., Am. J. Vet. Res. 46, 376–383 (1985), that most cases of canine KCS occur via autoimmune mechanisms.

Other diseases of the eye include phacoanaphylactic endophthalmitis and uveitis. These diseases can be located throughout the eye, in both the posterior and anterior chambers of the eye as well as in the vitreous body.

Uveitis, the inflamation of the uvea, is responsible for about 10% of the visual impairment in the United States. Phacoanaphylactic endophthalmitis is a human autoimmune disease.

Panuveitis refers to inflamation of the entire uveal (vascular) layer of the eye. Posterior uveitis generally refers to chorioentinitis, and anterior uveitis refers to iridocyclitis. The inflammatory products (i.e. cells, fibrins, excess proteins) of these inflammations are commonly found in the fluid spaces if the eye, i.e. anterior chamber, posterior chamber and vitreous space as well as infiltrating the tissue intimately involved in the inflammatory response. Uveitis may occur following surgical or traumatic injury to the eye; as a component of an autoimmune disorder, i.e. rheumatoid arthritis, Behcet's disease, ankylosing spondylitis, sarcoidosis; as an isolated immune mediated ocular disorder, i.e. pars planitis, iridocyclitis etc., unassociated with known etiologies; and following certain systemic diseases which cause antibody-antigen complexes to be deposited in the uveal tissues. Together these disorders represent the non-infectious uveitities.

The normal eye is protected from immune surveillance by blood barriers which do not allow free migration of cells or proteins into the eye. When the eye is injured or when vasculitis occurs, the internal ocular structures are exposed to the general immune system and frequently illicit autoimmune responses.

Phacoanaphylaxis is a severe form of uveitis in which the lens in the causative antigen. The lens proteins are normally secluded by the lens capsule since before birth. When these proteins are released into the eye by injury or by surgery or occasionally during cataract development, they can become intensely antigenic and incite an autoimmune response. If the response is moderate it is seen as chronic uveitis. If it is very fast in progression the eye becomes seriously inflamed in all segments. This latter response is named phacoanaphylaxis.

Methylthio-substituted cyclosporin A and other alkylthio-substituted cyclosporin A derivatives have been described in PCT application nos. 98-379455, 98-379456 and 98-379457 and have been found to be active against certain retroviruses, especially AIDS (acquired immunodeficiency syndrome) and ARC (AIDS-related complex) when administered orally, parenterally, rectally or by inhalation. In addition, they have generally been found to have only a very weak immunosuppressant action, and to show anti-retroviral activity at non-cytotoxic and non-cytostatic concentrations. These compounds are claimed to have a synergistic action with other agents active against retrovirus (such as inhibitors of reverse transcriptase, protease, integrase, HIV replication and nucleocapside).

Although these compounds are claimed to be effective against retroviruses, it has not been heretobefore suggested to administer any of these compounds to a patient in order to treat the ocular diseases described hereinabove. The present invention provides a method of treating a patient affected with such an ocular disorder by topically applying one or more of these compounds to the diseased eye.

SUMMARY OF THE INVENTION

Accordingly, a method in accordance with the present invention generally comprises the step of administering to an eye, a therapeutically effective amount of a compound selected from the group consisting of ((R)-methylthio-Sar)$^3$-(4'-hydroxy-MeLeu) cyclosporin A, ((R)-(Cyclo) alkylthio-Sar)$^3$-(4'-hydroxy-MeLeu)$^4$-cyclosporin A, and ((R)-(Cyclo)alkylthio-Sar)$^3$-cyclosporin A derivatives of the formulas described below, in order to treat an ocular disorder in the eye, for example, an aqueous deficient dry eye state, uveitis, or phacoanaphylactic endophthalmitis. The cyclosporin A derivatives utilized in the method of the present invention are disclosed in published PCT patent applications nos. 98-379455, 98-379456, and 98-379457, entitled New Methylthio-substituted Cyclosporin A derivative—Active Against Retro-viruses and Having Only Weak Immunosuppressant Action, Used in Treatment of AIDS, New Alkylthio-substituted Cyclosporin A derivatives—Active Against Retro-viruses and Having Only Weak Immunosuppressant Action, Used in Treatment of AIDS, and New Alkylthio-substituted Cyclosporin A derivatives—Active Against Retro-viruses and Having Only Weak Immunosuppressant Action, Used for Treating AIDS, respectively, which are hereby incorporated by reference in their entirety.

The objects and advantages of the present invention will be more clearly understood and appreciated with reference to the following detailed description.

DETAILED DESCRIPTION

The present invention provides a method for the treatment of uveitis and phacoanaphylactic endophthalmitis, in a patient suffering therefrom, as well as an aqueous deficient dry eye state, by topical application to the affected eye, of a cyclosporin derivative, selected from the group consisting of ((R)-methylthio-Sar)$^3$-(4'-hydroxy-MeLeu) cyclosporin A, ((R)-(Cyclo)alkylthio-Sar)$^3$-(4'-hydroxy-MeLeu)$^4$-cyclosporin A, and ((R)-(Cyclo)alkylthio-Sar)$^3$-cyclosporin A derivatives described below.

These cyclosporin derivatives are represented by the following general formulas (I), (II), and (III) respectively:

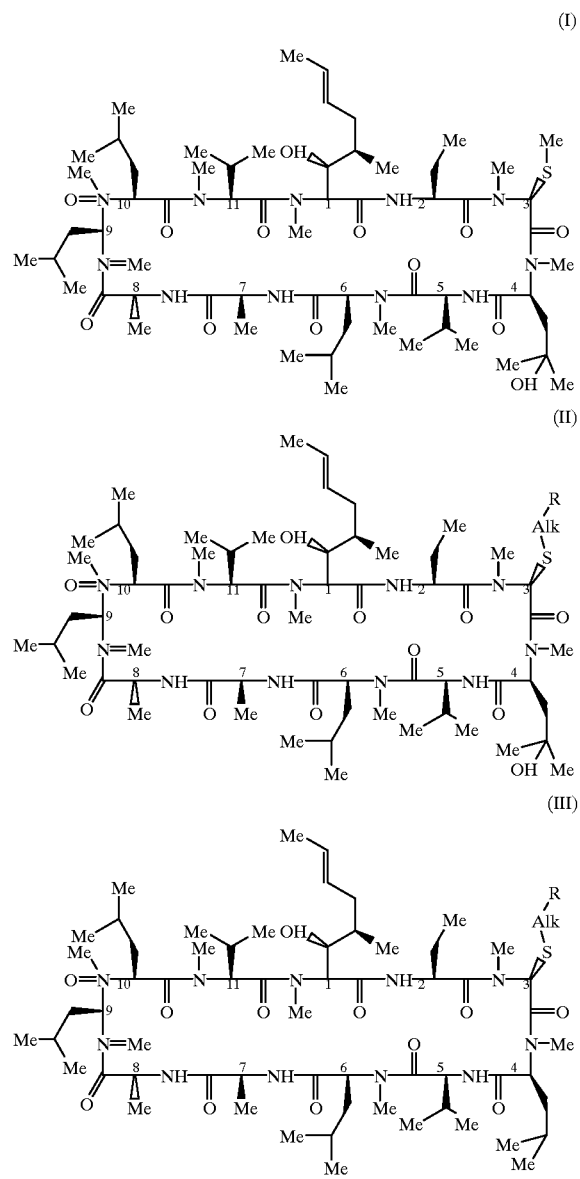

wherein Me is methyl; Alk is 2–6C alkylene or 3–6C cycloalkylene; R is OH, COOH, alkoxycarbonyl, —NR$_1$ R$_2$ or —N(R$_3$)—(CH$_2$)—NR$_1$R$_2$; wherein R$_1$, R$_2$is H, alkyl, 3–6C cycloalkyl, phenyl (optionally substituted by halo, alkoxy, alkoxycarbonyl, amino, alkylamino or dialkylamino), benzyl or saturated or unsaturated heterocyclyl having 5 or 6 members and 1–3 heteroatoms; or $NR_1R_2$ is a 5 or 6 membered heterocycle which may contain a further N, O or S heteroatom and may be alkylated; $R_3$ is H or alkyl and n is 2–4; and alkyl moieties contain 1–4C.

In accordance with the present invention, the cyclosporin A derivatives may be applied to an affected eye in any efficacious concentration, e.g., 0.01 to saturation (e.g. greater than 20 weight percent) in a pharmaceutically acceptable excipient. From 0.01 to 50 weight percent, preferably from 0.1 to 20 weight percent, of cyclosporin A derivatives in a pharmaceutically acceptable excipient may be used. Such pharmaceutically acceptable excipients are, for example, animal oil, vegetable oil, an appropriate organic or aqueous solvent, an artificial tear solution, a natural or synthetic polymer, or an appropriate membrane to encapsulate the cyclosporin A derivative.

Specific examples of these pharmaceutically acceptable excipients are olive oil, arachis oil, castor oil, mineral oil, petroleum jelly, dimethyl sulphoxide, chremophor, Miglyol 182 (commercially available from Dynamit Nobel Kay-Fries Chemical Company, Mont Vale, N.J.), an alcohol (e.g. ethanol, n-propyl alcohol, or iso-propyl alcohol), liposomes or liposome-like products or a silicone fluid. Preferred excipients are dimethyl sulphoxide and olive oil. Mixtures of at least two of any suitable excipients may be used.

Examples of artificial tear excipients which can be advantageously used in the practice of this invention are isotonic sodium chloride, cellulose ethers such as hydroxypropylmethylcellulose and hydroxyethylcellulose, polyvinyl alcohol and available artificial tea solutions.

An example of a useful polymeric excipient is a polyoxyethylated castor oil.

Examples of pharmaceutically acceptable membranes which can be advantageously used in the practice of this invention are microdone, an artificial lipid membrane, polyvinyl alcohol, or methylcellulose.

The cyclosporin A derivatives are advantageously administered topically as an ophthalmic drop (solution or suspension) or ophthalmic ointment containing an effective amount of the derivative. Concentrations of 0.01 to 50 weight percent, preferably 0.1 to 20 weight percent, of the cyclosporin A derivatives are used in the practice of the present invention.

In accordance with a method of the present invention, at least one of the cyclosporin A derivatives is administered topically in any quantity required to provide the degree of treatment needed. For example, 5 microliters to 1 milliliter of a solution, suspension, or ointment containing an effective amount of the cyclosporin A derivative, such as 0.01 to 50 weight percent, preferably 0.1 to 20 weight percent, of the cyclosporin A derivative is advantageously used.

Numerous advantages accrue with the practice of the present invention. The method of the present invention is useful in that it can locally prevent activation of a presystemic response. Topical administration of the cyclosporin A derivatives to a patient's tear deficient eye increases tear production in the eye. Thus, such treatment further serves to correct corneal and conjunctival disorders exacerbated by tear deficiency and KCS, such as corneal scarring, corneal ulceration, inflammation of the cornea or conjunctiva, filamentary keratisis, mucopurulent discharge and vascularization of the cornea. Furthermore, the cyclosporin A derivatives directly decrease the immune response and granulation and neovascularization.

Further objects of this invention, together with additional features contributing thereto and advantages accruing therefrom will be apparent from the following hypothetical examples of the invention.

EXAMPLE 1

The Effectiveness of Topical Application of the Cyclosporin A Derivatives of the Invention in Treating an Aqueous Deficient Dry Eye State is Demonstrated as Follows:

A one year old standard female poodle with conjunctivitis exhibits mild aqueous tear deficiency in both eyes. The dog has a Schirmer tear test value of 15 mm/minute in the right eye and 10 mm/minute in the left eye.

The Schirmer tear test is a test of aqueous tear production. The test depends upon observing the extent of wetting a strip of filter paper placed over the lower lid of an eye for a specified time. Standardized strips are commercially available. The strip is folded at a notched marking and then placed over the edge of the lateral one-third of the eyelid. The strip is then usually left in place for a period of time while the patient looks straight ahead in dim light.

The degree of wetting of the paper is measured in mm from the notch. For human patients, a normal end point is 5 mm of wetting at five minutes. For canine patients, the normal tear production is 14 to 20 mm at one minute.

The dog is treated with dexamethasone, a corticosteroid sometimes used as an antiinflammatory agent, by topical administration thereof in both eyes four times daily for nine weeks.

In addition to potential risks associated with such long term use of this antiinflammatory agent, it is predicted that the topical administration of dexamethasone, even when used in both eyes twice daily for nine weeks, may likely be without benefit.

Thus, in this example, the same dog at approximately six years old still exhibits conjunctivitis in both eyes. Due to the chronic nature of its condition and possibly due to the dog's normal aging, the dog may now have a lower Schirmer tear test value of 3 mm/minute in both eyes.

The same six year old dog is then treated by topical application 2% of a ((R)-methylthio-Sar)$^3$-(4'-hydroxy-MeLeu) cyclosporin A derivative of formula I in an olive oil solution in both eyes once daily without any other medications. After ten days, the dog shows markedly increased tear production.

The treatment by topical application of 2% of a ((R)-methylthio-Sar)$^3$-(4'-hydroxy-MeLeu) cyclosporin A derivative of formula I in an olive oil solution in both eyes once daily is continued for an additional three weeks. At this time, the dog exhibits plentiful aqueous tear production. The treatment is stopped for a period of one week and then restarted for a period of one week. After restarting the treatment, the dog may show even greater increased tear production.

In this case, a dog with chronic tear deficiency in which prior use of corticosteroids fails to improve tear secretion shows an increase in tear production with topical cyclosporin A derivatives. The increased tear production may continue only while cyclosporin A derivative therapy continues. When the treatment is stopped for a week, recurrence of tear deficiency may be found. However, tear production increases to normal levels after the treatment is restarted.

EXAMPLE 2

The Effectiveness of Topical Application of the Cyclosporin A Derivatives of the Invention in Treatment of Phacoanaphylactic Endophthalmitis is Demonstrated as Follows:

In this example, a lens induced granulomatous endophthalmitis (ELGE) model (See Marak, G. E. et al., *Ophthal.*

Res. (1978) 10:30) is reproduced in ⅛ control eyes of rats. Eyes treated topically with the cyclosporin A derivatives of Formula II uniformly fail to develop marked cellular infiltration following rupture of the lens capsule. Rats treated conventionally using systemic cyclosporine will show modest protection compared to untreated rats. Based on a prophylactic effect of topical application of the cyclosporin A derivatives of formula II against development of ELGE, penetration of the globe by the topical cyclosporin A derivatives in therapeutic levels is indicated.

Eleven female adult Wistar Furth rats are immunized subcutaneously on three occasions every two weeks with 1 ml of 50:50 mixture of 10 mg homologous lens protein in saline and Freund's complete adjuvant. Two weeks after the last immunization, the rats are anesthetized with Ketamine HCl 10 mg/kg intramuscularly. With the aid of a dissecting microscope, a sterile 26 g needle is introduced through the central cornea and a Z-shaped anterior lens capsule tear is formed by manipulating the needle in the right eye. Tobrex® ointment is applied post operatively and tetracycline 400 mg/liter is added to the drinking water.

Four rats serve as controls and receive no antiinflammatory drugs. Four rats receive 10 mg/kg of 2% cyclosporin A orally beginning two hours post-operatively. Three rats receive 15 μl of 2% of a ((R)-(Cyclo)alkylthio-Sar)$^3$-(4'-hydroxy-MeLeu)$^4$-cyclosporin A of Formula II in olive oil applied topically 9–12 times daily for three days following injury, then four times daily thereafter. After 7 days, the left eye capsules are torn as above in all rats.

All rats are examined periodically with a slit lamp or dissecting microscope. Fourteen days after the initial surgery, all rats are euthanized with halothane® anesthetic. Both eyes are fixed in formalin, processed by standard methods, and stained with hematoxylin and eosin.

It is predicted that immediately post-operatively, all rats develop a plasmoid aqueous and miosis lasting 48 to 72 hours. Several of the eight untreated eyes continue to develop severe uveitis beginning with hypopyon and corneal edema. Some of these untreated eyes also develop secondary glaucoma with buphthalmos. Progression continues with the development of corneal abcessation, neovascularization and panophthalmitis. Some eyes may progress to a phthesis bulbi. Histopathology of these eyes reveal an aseptic gramulomatous panophthalmitis. A zonal distribution of neutrophilis and macrophages occurs around the ruptured lens capsule where early cataractrous changes were evident. A cyclictic membrane forms behind the lenses. The anterior chamber, iris, vitreous humour and retina are densely infiltrated with lymphocytes. On histopathologic examination, several untreated eyes have moderate, acute anterior uveitis; however, it is predicted that some untreated eyes may have no inflammation at seven or fourteen days post injury.

In contrast, none of the six eyes treated with topical ((R)-(Cyclo)alkylthio-Sar)$^3$-(4'-hydroxy-MeLeu)$^4$-cyclosporin A derivative of Formula II develop any prolonged or destructive inflammation.

The rats given oral cyclosporine may develop uveitis intermediate in intensity between controlled and topically treated eyes.

EXAMPLE 3

The Effectiveness of Topical Application of the Cyclosporin A Derivatives of the Invention in Treating Uveitis is Demonstrated as Follows:

Sixteen rabbits, 32 eyes are injected intravitreally on day 1 with 500 micrograms of human serum albumin. Eight rabbits receive no treatment. The other rabbits receive 10 microliters of 2% of a ((R)-(Cyclo)alkylthio-Sar)$^3$-(4'-hydroxy-MeLeu)$^4$-cyclosporin A derivative of Formula II in olive oil applied topically to both eyes four times daily beginning 1 hour after albumin injection. The degree of intraocular inflammation produced is graded clinically three time a week for three weeks. The scale used to evaluate the eyes is given below:

| Scheme for Grading Uveitis in Animals injected with Human Serum Albumin | | | | | |
|---|---|---|---|---|---|
| Clinical Observation | 0 | +1 | +2 | +3 | +4 |
| Ciliary-scleral injection | none | trace | mild | moderate | severe |
| Corneal clarity | clear | trace edema | mild edema | moderate | severe |
| Iris injection | none, pupil normal | trace | mild | moderate | severe, pupil fixed |
| Anterior chamber haze | clear | trace | mild | moderate, ± few KP's | Opaque, ± many KP's |
| Vitreous & retina | Chorioretinal detail sharp | Chorioretinal detail visible but blurred | fair red reflex | poor red reflex | no red reflex |

The degree of inflammation, 1–4 of each regiment of the eye is summed on each day, giving a possible range of inflammation of 0–20 per day. A marked difference in clinical severity of inflammation between eyes treated with the cyclosporin A derivative of Formula II and control eyes is found.

In a broader aspect of the present invention, the cyclosporin A derivatives of the present invention may be useful in treating other disorders of the eye, for example a disorder caused by excessive immune activity in the anterior segment, posterior segment or the vitreous body of an eye, when administered in an amount sufficient to reduce said immune activity.

Although there has been hereinabove described a method for ocular treatment using certain cyclosporin A derivatives, in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for enhancing or restoring lacrimal gland tearing in an eye, the method comprising administering topically to the eye, in a pharmaceutically acceptable excipient, a methyl thio-substituted or other alkyl thio-substituted cyclosporin A derivative selected from the group consisting of compounds represented by the general formulas:

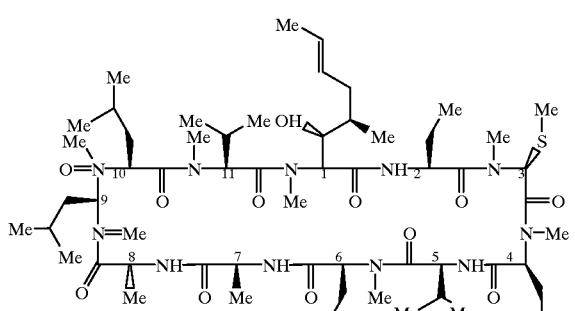

(I)

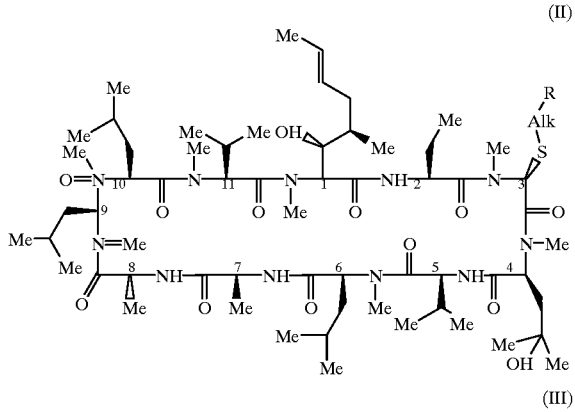

(II)

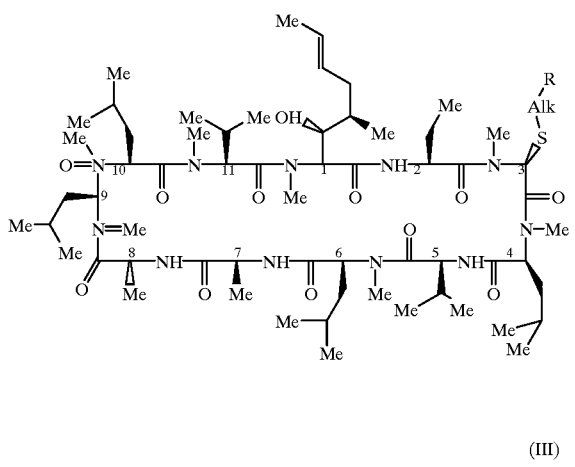

(III)

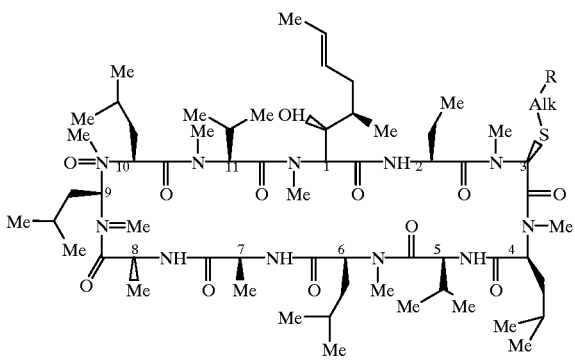

(III)

wherein Me is methyl; Alk is 2–6C alkylene or 3–6C cycloalkylene; R is OH, COOH, alkoxycarbonyl, —NR₁R₂ or —N(R₃)—(CH₂)ₙ—NR₁R₂; wherein R₁, R₂ is H, alkyl, 3–6C cycloalkyl, phenyl (optionally substituted by halo, alkoxy, alkoxycarbonyl, amino, alkylamino or dialkylamino), benzyl or saturated or unsaturated heterocyclyl having 5 or 6 members and 1–3 heteroatoms; or NR₁R₂ is a 5 or 6 membered heterocycle which may contain a further N, O or S heteroatom and may be alkylated; R₃ is H or alkyl and n is 2–4; and alkyl moieties contain 1–4C.

2. The method according to claim 1 wherein the compound is administered as a solution, suspension or ointment comprising 0.01 to 50 weight percent of the compound.

3. The method according to claim 2 wherein the compound is administered in an amount of 0.1 to 20 weight percent.

4. The method according to claim 1 wherein the pharmaceutically acceptable excipient is selected from the group consisting of olive oil, arachis oil, castor oil, polyoxyethylated castor oil, mineral oil, petroleum jelly, dimethyl sulphoxide, an alcohol, liposome, silicone fluid and mixtures thereof.

5. The method of claim 4 wherein the pharmaceutically acceptable excipient is dimethyl sulphoxide.

6. A method for treating a disorder exacerbated by deficient tear production in a patient, the method comprising administering topically to the eye, in a pharmaceutically acceptable excipient, a methyl thio-substituted or other alkyl thio-substituted cyclosporin A derivative selected from the group consisting of compounds represented by the general formulas:

(I)

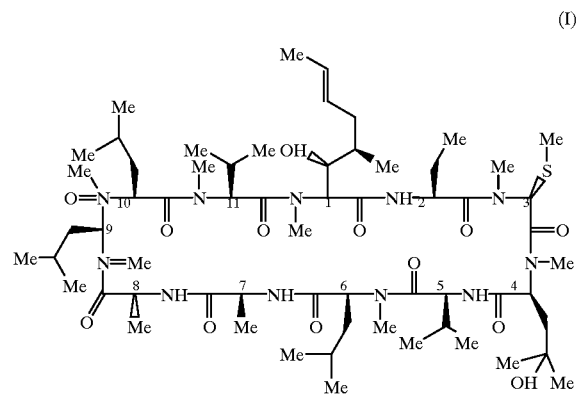

(II)

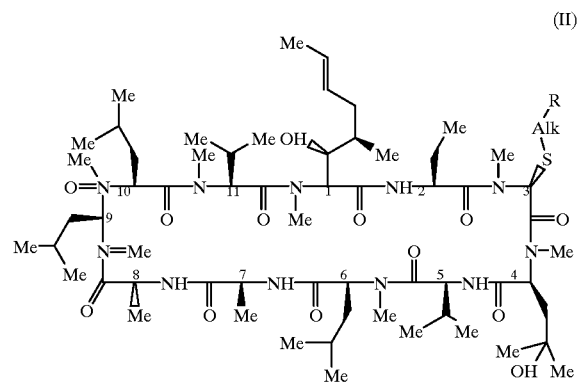

-continued (III)

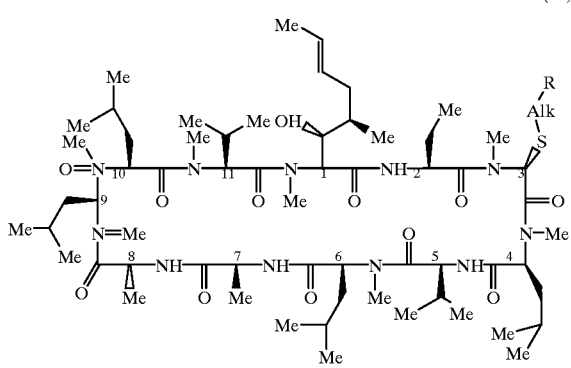

wherein Me is methyl; Alk is 2–6C alkylene or 3–6C cycloalkylene; R is OH, COOH, alkoxycarbonyl, —NR$_1$R$_2$ or —N(R$_3$)—(CH$_2$)$_n$—NR$_1$R$_2$; wherein R$_1$, R$_2$ is H, alkyl, 3–6C cycloalkyl, phenyl (optionally substituted by halo, alkoxy, alkoxycarbonyl, amino, alkylamnino or dialkylamino), benzyl or saturated or unsaturated heterocyclyl having 5 or 6 members and 1–3 heteroatoms; or NR$_1$R$_2$ is a 5 or 6 membered heterocycle which may contain a further N, O or S heteroatom and may be alkylated; R$_3$ is H or alkyl and n is 2–4; and alkyl moieties contain 1–4C.

7. The method according to claim 6 wherein the compound is administered as a solution, suspension or ointment comprising 0.01 to 50 weight percent of the compound.

8. The method according to claim 7 wherein the compound is administered in an amount of 0.1 to 20 weight percent.

9. The method according to claim 6 wherein the pharmaceutically acceptable excipient is selected from the group consisting of olive oil, arachis oil, castor oil, polyoxyethylated castor oil, mineral oil, petroleum jelly, dimethyl sulphoxide, an alcohol, liposome, silicone fluid and mixtures thereof.

10. The method of claim 9 wherein the pharmaceutically acceptable excipient is dimethyl sulphoxide.

* * * * *